United States Patent [19]

Kano et al.

[11] Patent Number: 5,066,465
[45] Date of Patent: Nov. 19, 1991

[54] REACTION APPARATUS

[75] Inventors: Tokio Kano, Nesconset, N.Y.; Toshinobu Niimura, Hachioji, Japan; Hiroyuki Yonekawa, St. James, N.Y.

[73] Assignee: Olympus Optical Co., Ltd., Tokyo, Japan

[21] Appl. No.: 457,289

[22] Filed: Dec. 27, 1989

[51] Int. Cl.$^5$ ............................................. B01N 21/01
[52] U.S. Cl. .................................. 422/58; 422/102; 422/57; 436/520; 436/533; 436/539; 436/541; 424/11
[58] Field of Search ............................ 422/102, 58, 57; 436/520, 533, 539, 541; 424/11

[56] References Cited

U.S. PATENT DOCUMENTS 4,303,616 12/1981 Kano et al. .
4,427,781 1/1984 Masson et al. .
4,608,246 8/1986 Bayer .
4,756,884 7/1988 Hillman et al. .................. 422/73

FOREIGN PATENT DOCUMENTS

61-44268 10/1986 Japan .

Primary Examiner—David L. Lacey
Assistant Examiner—Abanti B. Singla
Attorney, Agent, or Firm—Frishauf, Holtz, Goodman & Woodward

[57] ABSTRACT

A reaction apparatus with sample inlet channel of suitable cross-sectional area for aspirating a sample into the interior of the apparatus by capillarity, a recess provided on the inner wall of the sample inlet channel, and a transparent plate with a flat surface arranged opposite the recess. The recess has sloping walls, and may for example, have a conical or hemispherical form. The recess may moreover be a V-shaped or U-shaped groove. Further, the inner wall of the recess may be coated with antibodies or antigens.

14 Claims, 6 Drawing Sheets

REACTION APPARATUS

BACKGROUND OF THE INVENTION

1. Field of the Invention

This invention concerns a reaction vessel for carrying out agglutination reactions, and in particular, a reaction vessel used for hemanalysis involving immunological antigen-antibody reactions.

2. Description of the Related Art

Conventional reaction vessels used for detections by using immunological agglutination reactions are, for example, of the type disclosed in U.S. Pat. No. 4,303,616. These reaction vessels are usually referred to by the generic name of microplates.

One detection method using this kind of reaction vessel is particle agglutination method whereby antigens or antibodies in the sample are detected based on an immunological agglutination reaction. In this method, a specific marker particle is used, and antigens or antibodies which conjugate specifically to the substance being measured are coated on the surface of the particle. To detect viruses in blood, for example, a man made marker particle on which the antibodies against for the virus are coated is used. The method is carried out using said reaction vessel as follows. First, said marker particles are mixed with the sample in the reaction vessel, an immunological reaction takes place with the antigens or antibodies in the sample, and the marker particles collect on one of the walls (for example the bottom) of the reaction vessel. The particles collected on the wall of the vessel however have a different distribution pattern depending on whether there was or was not an immunological reaction with the substance being measured in the sample. It is therefore possible to determine a positive or negative reaction for the substance from the distribution pattern of marker particles on the wall of the vessel.

Another method, the mixed agglutination method, was reported by A. S. Wiener and M. H. Herman. This method was subsequently improved in stages so that it could even determine blood group. To determine blood group, for example, the following procedure is carried out using said reaction vessel. First, suitable quantities of a fixed concentration of red blood cells and a fixed dilution of serum are mixed in the reaction vessel, and allowed to stand for a certain time. As in the method described above, the distribution pattern of sedimented red blood cells is different according to whether there was or was not an immunological reaction between antigens on the red blood cells, and antibodies in the serum. It is therefore possible to determine a positive or negative reaction from the distribution pattern of sedimented red blood cells.

In the reaction vessel described in U.S. Pat. No. 4,303,616, however, at least about 50 $\mu$l of liquid is required to form a stable and accurate distribution pattern. If the quantity of liquid is less than 50 $\mu$l, the sedimentation of particles is disturbed and to be irregular due to surface tension, and the distribution pattern does not form correctly. For this reason, the depth of reaction solution in this reaction vessel requires no less than 3 mm. It is moreover for this reason that the distribution pattern takes a long time to form. In other words, the particles such as red blood cells which form the distribution pattern have to move over a considerable distance, and as a result, the time required to form the pattern is long.

The above problem, namely that the distribution pattern is not formed correctly when the quantity of liquid is too small, can be overcome to some extent by making the internal diameter of the reaction vessel smaller. In this case, however, the surface tension between the reaction solution and the walls of the reaction vessel comes into play, and the liquid surface again sinks or rises irregularly. The result is that it becomes difficult to measure the distribution pattern which is formed accurately.

Further, if the internal diameter of the vessel is made smaller so that the quantity of liquid becomes smaller, the time required to form the distribution pattern is shorter, but the problem then arises that it is necessary to handle minute quantities of reagent. In particular, when the quantity of liquid is no greater than 5 $\mu$l, it becomes extremely difficult technically to pipette reagents accurately with high reproducibility.

SUMMARY OF THE INVENTION

This invention aims to provide a reaction vessel for agglutination reactions, wherein an accurate distribution pattern of sedimented particles is formed in a short time, and the distribution pattern obtained can be determined accurately.

Said objectives are achieved by a reaction vessel provided with a sample inlet channel of cross-sectional area suitable for aspirating the sample into the interior of the reaction vessel by capillarity, a recess arranged on the inner wall of said inlet channel, and a transparent plate with a flat surface opposite said recess.

Said sample inlet channel generally comprises a lower plate in which said recess is formed, a transparent plate arranged such that its flat surface faces the recess on the lower plate, and spacers inserted between said lower plate and said transparent plate.

In the reaction vessel according to this invention, the sample is introduced by means of capillarity. From the opening of the sample inlet channel, the sample moves under capillarity to reach the recess on the inner wall of the channel, and for this reason, the cross-sectional area of the sample inlet channel must be suitable for aspirating the sample into the interior of the vessel by capillarity. This cross-sectional area varies according to the sample being measured, but if the sample consists of blood components, it is preferably 0.2-5 mm$^2$.

The occurrence or non-occurrence of an agglutination reaction is observed in the recess on the inner wall of the sample inlet channel through the transparent plate opposite the recess. This recess may take several forms. It may, for example, be conical or hemispherical, or it may be a groove of V-shaped or U-shaped cross section. There may also be several recesses in the sample inlet channel.

DETAILED DESCRIPTION OF THE PREFERRED EMBODIMENTS

As described above, in the reaction vessel of this invention, there is a flat wall opposite the sample inlet channel above the recess at a very small distance away which can be covered by capillarity. The depth of sample in the recess, which is where the measurement is made, is limited by the opposite wall and is very shallow. The distance over which the sedimented particles move is therefore very much reduced, and the distribution pattern is formed in a short time. Further, as the liquid surface of the sample is in contact with the flat opposite wall, the liquid surface is kept flat, and there is no disturbance of the distribution pattern of the particles. Moreover, as the liquid surface of the sample can be kept flat, the recess can be made very small so that the distance over which the sedimented particles move can be reduced even further.

Further, the sample may be introduced by means of capillarity, for example, by dropping it into the opening of the sample inlet channel. In this case, the quantity of liquid in the recess is always constant regardless of the quantity dropped in. It is not therefore especially necessary to pipette small quantities precisely.

We shall now describe one embodiment of reaction vessel in this invention with reference to the drawings.

Figure 1A:
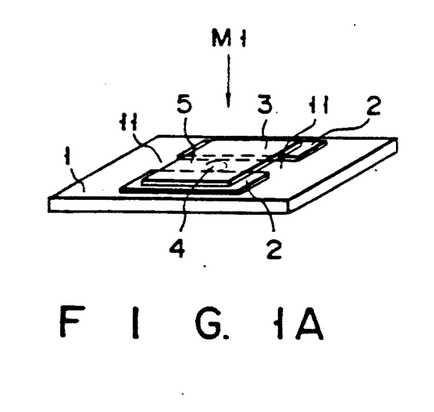
FIG. 1A is a perspective view showing one embodiment of the reaction vessel according to this invention.
Figure 1B:
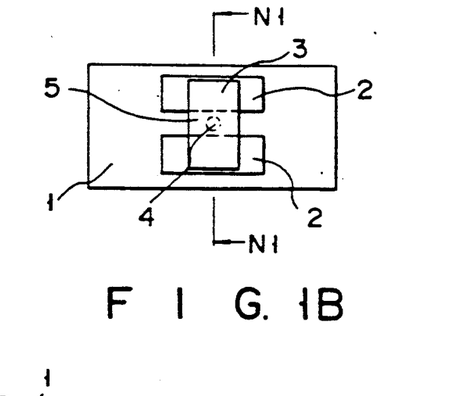
FIG. 1B is a plan view seen from direction M1 of the reaction vessel shown in FIG. 1A.
Figure 1C:
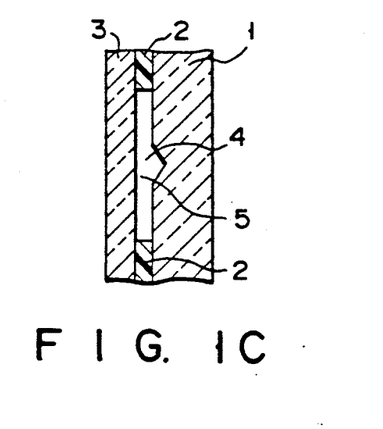
FIG. 1C is a cross-section through N1 of the reaction vessel shown in FIG. 1B.

FIG. 1A is a perspective view of the reaction vessel according to this invention; FIG. 1B is a plan view from the direction M1 of the reaction vessel shown in FIG. 1A; and FIG. 1C is cross-section through N1 of the reaction vessel shown in FIG. 1A and FIG. 1B. As can be seen from these figures, the lower plate 1 and upper plate 3 are arranged substantially parallel on either side of 2 spacers 2. Lower plate 1 and upper plate 3 are both made of transparent parts, and a recess of conical shape is provided in lower plate 1. Part 5 surrounded by lower plate 1, upper plate 3 and the 2 spacers 2 is a sample inlet channel for introducing the sample, and it is also the reaction zone where the agglutination reaction takes place. The 2 sides where the spacers are not inserted constitute the sample inlet port 11, into which the sample is either injected or aspirated.

In this reaction vessel, it is preferable that the thickness of the spacers 2, i.e., the distance between lower plate 1 and upper plate 3, is 0.05-1.0 mm, and that the distance between the spacers 2 is 0.1-5.0 mm. Further, it is preferable that the diameter of the conical recess 4 on lower plate 1 is 0.1-1.0 mm, that its depth is 0.02-1.0 mm, and that the angle made by 2 generators of conical recess 4 shown in FIG. 1C is 60°-160°.

This reaction vessel may be used to establish whether an agglutination reaction has or has not occurred. In the case where, for example, this reaction vessel is used to determine the occurrence of a reaction between blood cells and antibodies in serum, the following procedure is carried out.

Figure 2A:
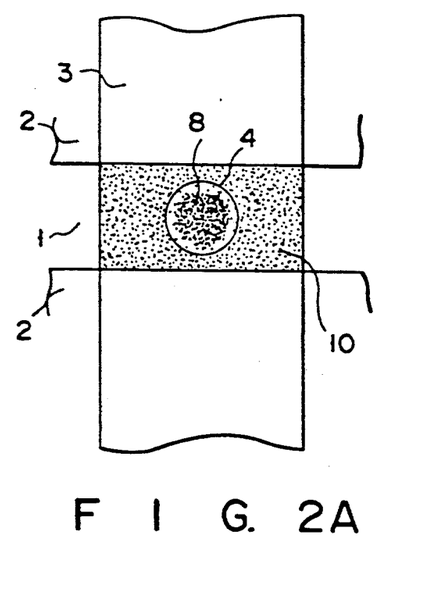
FIG. 2A is a sediment particle distribution pattern obtained when there was an agglutination reaction in an agglutination test carried out using the reaction vessel shown in FIGS. 1A-1C.
Figure 2B:
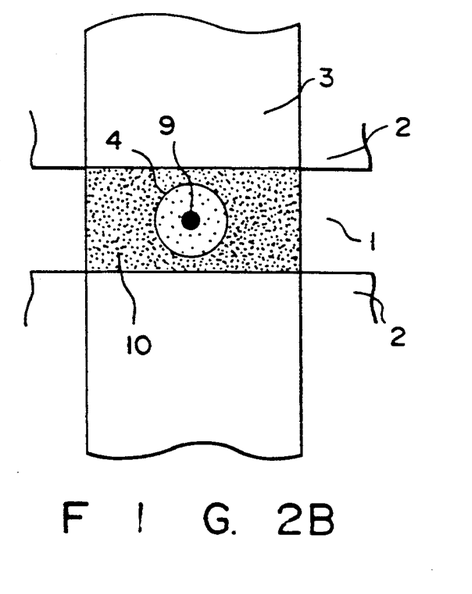
FIG. 2B is a sediment particle distribution pattern obtained when there was no agglutination reaction in an agglutination test carried out using the reaction vessel shown in FIGS. 1A-1C.
Figure 3A:
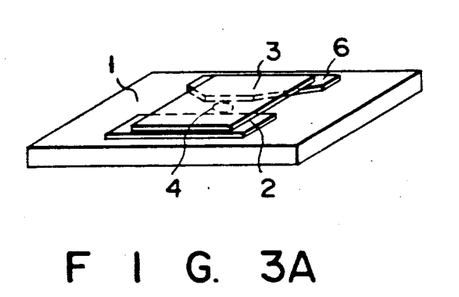
FIG. 3A is a perspective view of a modification with a different shape of spacer.
Figure 3B:
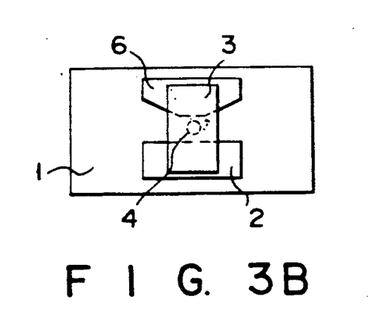
FIG. 3B is a plan view of the reaction vessel shown in FIG. 3A.
Figure 4A:
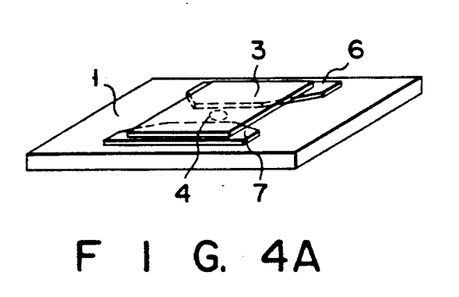
FIG. 4A is a perspective view of another modification with a different shape of spacer.
Figure 4B:
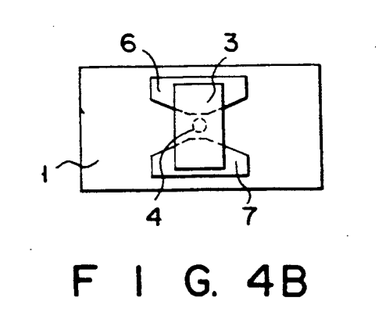
FIG. 4B is a plan view of the reaction vessel shown in FIG. 4A.

First, a fixed concentration of a blood cell suspension and a fixed dilution of serum are mixed in a test tube. The mixture is then aspirated by a pipette, and a suitable quantity is dropped to sample inlet port 11. The mixed solution dropped then spreads by capillarity throughout the reaction zone 5. The reaction vessel is allowed to stand undisturbed for a certain time, and blood cells sediment out on lower plate 1 of reaction zone 5. The distribution pattern of cells formed in conical recess 4 differs according to whether an antigen-antibody reaction has or has not occurred, and it is therefore possible to verify the occurrence of this reaction. If the blood cells agglutinated due to an antigen-antibody reaction, the cells form a positive pattern 8 wherein they are spread uniformly on the sloping walls and bottom of recess 4, as shown in FIG. 2A. If on the other hand no reaction occurred and the blood cells did not agglutinate, the cells slide down the sloping walls of recess 4 to form a negative pattern 9 wherein they are concentrated in the center of the cone, as shown in FIG. 2B.

On the flat area 10 outside recess 4 of reaction zone 5, the cells sediment uniformly, and the concentration of the blood suspension used in the reaction can therefore be measured. The cell distribution pattern can also be corrected based on this blood cell concentration.

Concentric grooves may be provided on the side walls of conical recess 4 as disclosed in Japanese patent application No. 54-77643, but if recess 4 is sufficiently small, there is no particular need for such grooves. The meaning of "sufficiently small" in this context is that the diameter of recess 4 is within several hundred times the particle diameter, and if the particles are red blood cells, this corresponds to a diameter within approximately 400 μm.

If recess 4 is made small in order to form the distribution pattern in a short time, the pattern will also be small and difficult to observe with the naked eye. In this case, the pattern may be observed magnified with the aid of a lens or other device.

In the reaction vessel shown in FIGS. 1A–1C, rectangular spacers may be used. The shape of the spacers is however not limited to rectangular, and spacers such as a spacer 6 or 7 having the shapes shown in FIGS. 3A–4B may also be used. Using spacers of this shape widens the sample inlet port so that pipetting of sample becomes easier.

The shape of recess 4 on lower plate 1 of the reaction vessel is moreover not limited to conical, and any shape may be used provided the sloping walls of the recess have a suitable angle of slope. An example of another possible shape is hemispherical.

Figure 5A:
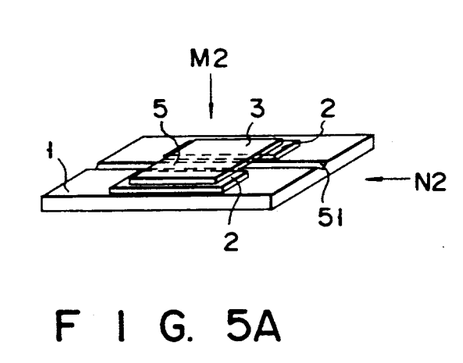
FIG. 5A is a perspective view of a modification having a groove instead of a recess.
Figure 5B:
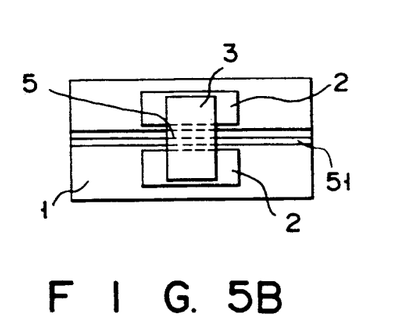
FIG. 5B is a plan view seen from direction M2 of the reaction vessel shown in FIG. 5A.
Figure 5C:
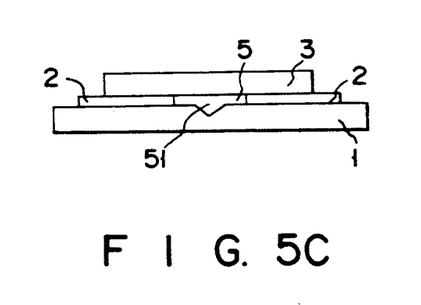
FIG. 5C is a plan view seen from direction N2 of the reaction vessel shown in FIG. 5A.

Further, as shown in FIGS. 5A–5C, a V-shaped groove 51 may be provided instead of recess 4. With this type of reaction vessel, the pipetting of blood cell suspensions is particularly easy.

Figure 6A:
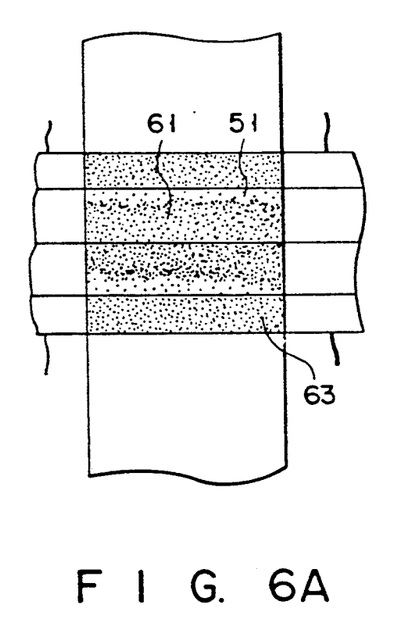
FIG. 6A is a sediment particle distribution pattern obtained when there was an agglutination reaction in an agglutination test carried out using the reaction vessel shown in FIGS. 5A-5C.
Figure 6B:
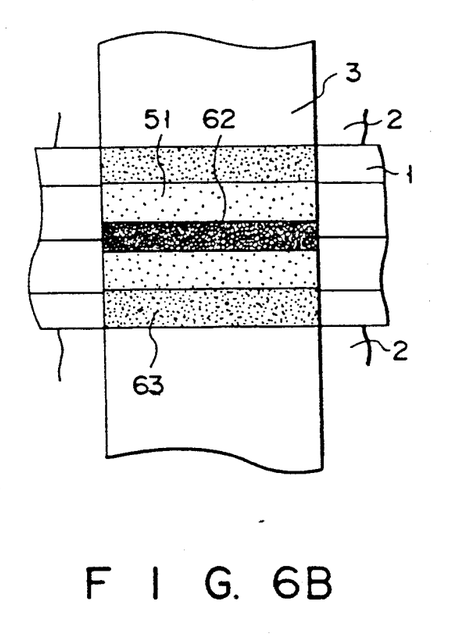
FIG. 6B is a sediment particle distribution pattern obtained when there was no agglutination reaction in an agglutination test carried out using the reaction vessel shown in FIGS. 5A-5C.

The occurrence or non-occurrence of an agglutination reaction may also be established in the reaction vessel shown in FIGS. 5A–5C by the same method as is used with the reaction vessel shown in FIGS. 1A–1C. If a test is carried out to establish the occurrence or non-occurrence of a reaction of blood cells with antibodies in serum by the method described above, for example, a distribution pattern shown in FIG. 6A or 6B is obtained depending on whether the reaction took place. FIG. 6A is a drawing of a positive pattern 61 in the case where the particles agglutinated due particles are spread over the whole of the sloping surface of V-shaped groove 51. FIG. 6B is a drawing of a negative pattern 62 in the case where an antigen-antibody reaction did not occur, wherein almost all the blood cells have collected in the bottom of V-shaped groove 51. Further, the sedimented particles 63 on lower plate 1 outside V-shaped groove 51 are uniformly distributed in both cases.

In addition to the reaction vessel shown in FIGS. 5A–5C, the reaction vessel with a V-shaped groove on lower plate 1 may also be of the type shown in FIGS. 7A–10C.

Figure 7A:
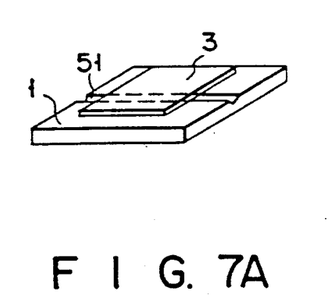
FIG. 7A is a perspective view of another modification with a groove instead of a recess.
Figure 7B:
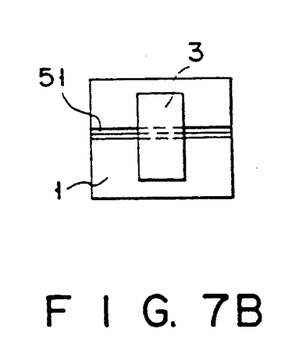
FIG. 7B is a plan view of the reaction vessel shown in FIG. 7A.
Figure 7C:
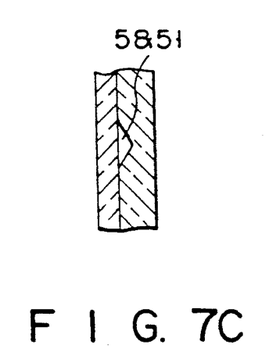
FIG. 7C is a cross-section of the reaction vessel shown in FIG. 7A.

The reaction vessel shown in FIGS. 7A–7C is same as that in FIGS. 5A–5C excepting that the spacers 2 have been removed, and the upper plate 2 is fixed directly to the lower plate 1. In this case, V-shaped groove 51 also functions as the sample inlet channel. In this type of reaction vessel, it is not possible to measure the quantity of particles sedimented, and only the particle distribution pattern can be observed.

Figure 8A:
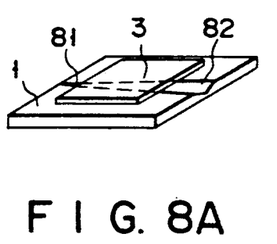
FIG. 8A is a plan view of another modification with a groove instead of a recess.
Figure 8B:
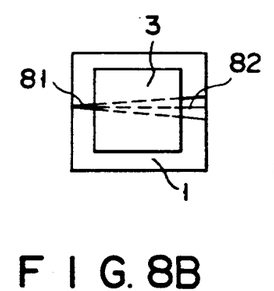
FIG. 8B is a plan view of the reaction vessel shown in FIG. 8A.
Figure 8C:
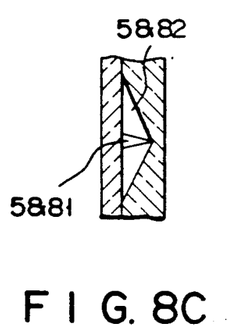
FIG. 8C is a cross-section of the reaction vessel shown in FIG. 8A.

In the reaction vessel shown in FIGS. 8A to 8C, a V-shaped groove is provided wherein the angle of slope of the sloping surface of the groove varies continuously. The angle of slope of the V-shaped groove varies continuously from a steep slope in part 81 of the groove, to a gentle slope in part 82 of the groove. In this type of reaction vessel, the cohesive force may be measured. The particles will tend to remain on the wall surface where the slope is steeper when the cohesive force is stronger, so the more particles which have collected near part 81 of the groove, the stronger the cohesive force.

Figure 9A:
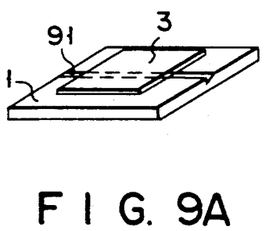
FIG. 9A is a plan view of a further modification with a groove instead of a recess.
Figure 9B:
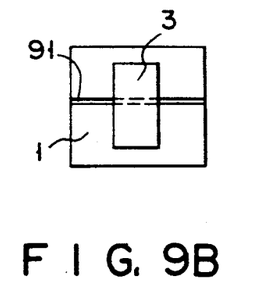
FIG. 9B is a plan view of the reaction vessel shown in FIG. 9A.
Figure 9C:
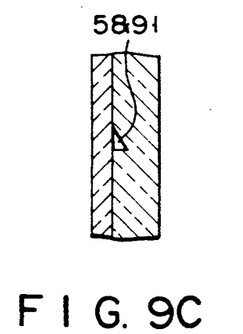
FIG. 9C is a cross-section of the reaction vessel shown in FIG. 9A.

In the reaction vessel shown in FIGS. 9A–9C, a groove 91 of which shape is half of V-shape is provided on lower plate 1.

Figure 10A:
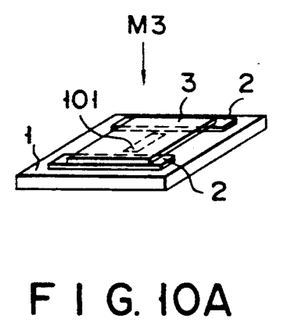
FIG. 10A is a perspective view of another modification with a groove extending rectangularly to the sample inlet channel.
Figure 10B:
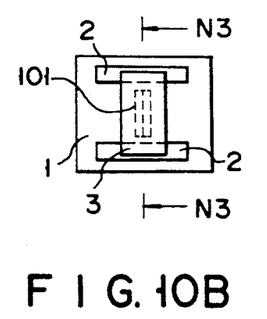
FIG. 10B is a plan view of the reaction vessel shown in FIG. 10A.
Figure 10C:
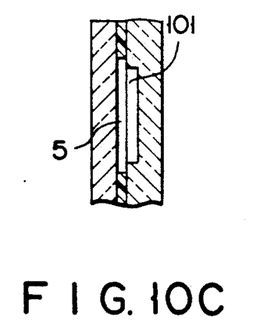
FIG. 10C is a cross-section through N3 of the reaction vessel shown in FIG. 10B.

In the reaction vessel shown in FIGS. 10A–10C, a V-shaped groove 101 is provided rectangularly to the sample inlet channel.

In the reaction vessel provided with a groove instead of a recess on lower plate 1, therefore, the groove need not necessarily be V-shaped, and may for example be U-shaped.

Further, the number of recesses or grooves provided in reaction zone 5 need not be limited to one, and several grooves or recesses may be provided. By providing several recesses or grooves, several distribution patterns may be formed simultaneously, and the precision of measurement may thus be increased.

We shall now describe some agglutination tests using the reaction vessel of this invention.

EXAMPLE 1

Determination of Human ABO Blood Group

Figure 11:
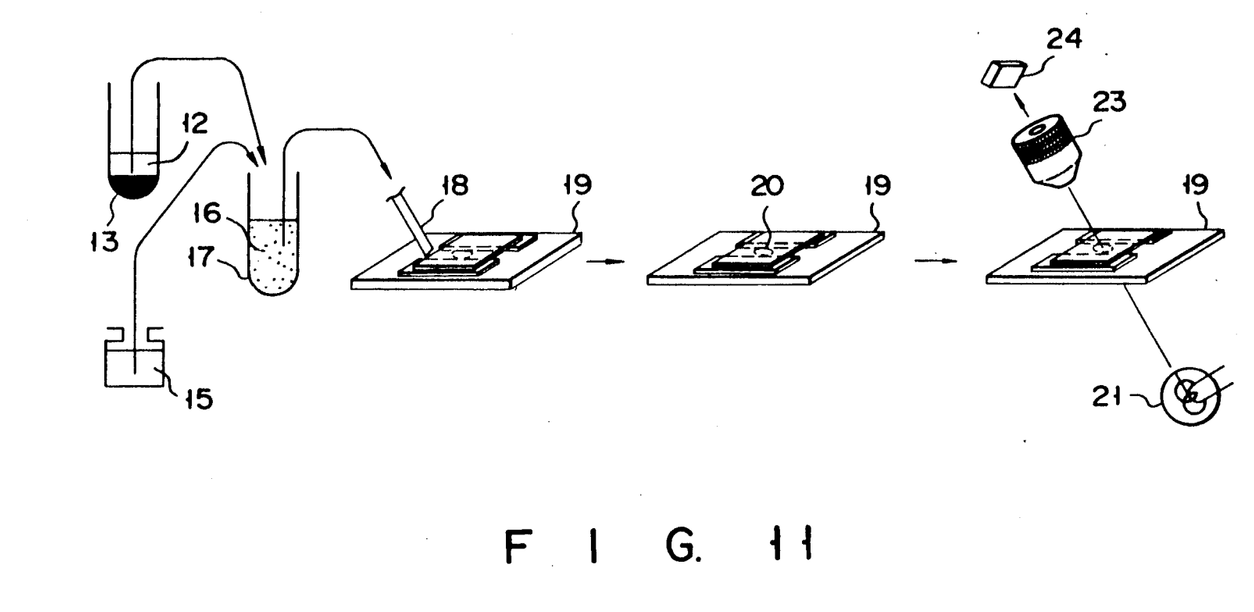
FIG. 11 is a view showing a process in an agglutination test using the reaction vessel shown in FIGS. 1A-1C.

We shall describe the determination of human ABO blood group using the reaction vessel of FIGS. 1A–1C with reference to FIG. 11.

First, a sample of blood is separated into a blood cell component 13 and blood serum component 12 by centrifugation or another suitable method. If the blood was treated with an anticoagulant such as heparin, the blood serum component 12 will be plasma. Next, 2 μl of the blood cell component 13 and 118 μl of a previously prepared solution 15 are mixed in a test tube 17, and initially prereacted together. This solution 15 consists of an anti-A serum dilution prepared by diluting standard anti-A serum (Orso Co.) to 1/30 with physiological saline. After the preliminary reaction, 5 μl of blood cell suspension 16 are pipetted by means of pipette 18 into reaction zone 5 of reaction vessel 19. Using a reaction vessel wherein the distance between lower plate 1 and upper plate 3 is 80 μm, the length of the sloping wall of conical recess 4 is 500 μm, and the depth of recess 4 is 250 μm, sedimentation of all human red blood cells on the bottom of recess 4 is complete in about 10 minutes. After pipetting blood cell suspension 16, therefore, the reaction vessel is left in an incubator at 36° C. for about 10 minutes.

After the reaction is complete, the reaction vessel 19 is transferred to the measurement area. The measurement area comprises a light source 21, and a microscope optical system 23 to observe the blood cell distribution pattern magnified, and it also has a photo sensor 24 to image the magnified blood cell distribution in the reaction zone. The occurrence or non-occurrence of an antigen-antibody reaction is determined by magnifying the reaction zone 5 of reaction vessel 19 by means of optical system 23, and observing the blood cell distribution pattern. Alternatively, instead of observing the pattern with the naked eye, the image obtained by photo sensor 24 may be analyzed by a computer to determine the occurrence or non-occurrence of the reaction.

If the measured blood cell distribution has a pattern of the type shown in FIG. 2A, it indicates that there are A antigens on the surface of the blood cells in the sample, and that the blood cells have agglutinated due to anti-A antibodies. If on the other hand the blood cell distribution has a pattern of the type shown in FIG. 2B, it indicates that there are no A antigens on the surface of the blood cells in the sample, and that the cells moved freely down the sloping walls of conical recess 4.

The reactivity of the sample with respect to anti-B serum is measured in the same way, and from its measured reactivity with respect to anti-A serum and anti-B serum, the blood group of the sample can be determined. If the blood cells in the sample showed an antigen-antibody reaction with respect to both anti-A serum and anti-B serum, the blood group of the sample is AB; if there was a reaction only with respect to anti-A serum, the blood group of the sample is A; if there was a reaction only with respect to anti-B serum, the blood group of the sample is B; while if there was no reaction to either serum, the blood group of the sample is O.

The determination of blood group, which previously required 60 minutes, can be accomplished in about 10 minutes using the reaction vessel of this invention.

EXAMPLE 2

Assay for Anti-HIV Antibody

We shall describe an assay for anti-HIV antibody using the reaction vessel of FIGS. 1A–1C.

First, a sample of blood is separated into a blood cell component 13 and blood serum component 12 by centrifugation or another suitable method. If the blood was treated with an anticoagulant such as heparin, the blood serum component 12 will be plasma. After separation, 2 $\mu$l of the supernatant blood serum component 12 and 5 $\mu$l of a previously prepared solution 15 are mixed in a test tube 17, and initially prereacted together. This solution 15 consists of sensitized particles diluted to 1.0% (v/v) with physiological saline, organically synthesized peptides having an identical amino acid sequence to HIV antigen being coated on the surface of these sensitized particles. The sensitized particles may consist of artificial particles of polystyrene or gelatin which have been modified chemically, animal red blood cells fixated by glutaraldehyde or the like, or similar particles. The antigen used to sensitize the particles may be an inactivated virus, or a recombinant protein produced by *Escherichia coli* or the like using gene manipulation techniques. When the preliminary reaction is complete, 25 $\mu$l of a suspension of the sensitized particles is pipetted into reaction zone 5 of reaction vessel 19 by means of pipette 18, and the suspension is incubated at room temperature for 10 min.

After the reaction is complete, the distribution of particles which have sedimented in zone 5 of reaction vessel 19 is observed using the same method as in Example 1. If the measured particle distribution gives a pattern of the type shown in FIG. 2A, it indicates that there are anti-HIV antibodies in the serum of the sample, and that the particles have agglutinated due to the anti-HIV antibodies. If on the other hand the particle distribution gives a pattern of the type shown in FIG. 2B, it indicates that there are no antibodies in the sample reacting to the surface antigens of the sensitized particles.

By varying the type of antigen coated on the particles, an assay may be carried out for viruses or bacteria other than HIV such as HTLV-1, HB or gonococcus. Further, using antibody-sensitized particles, an assay for antigen may be carried out for HBs, drugs or cancer markers. Further, if particles of several different colors are made to combine respectively with different antibodies or antigens, and for example a color CCD camera is used as photo sensor 24, assays for several antibodies or antigens may be carried out in one operation.

Whereas the assay for anti-HIV antibody using the conventional agglutination method required 120 min, an assay can be carried out in 10 min using the reaction vessel of this invention. Moreover, the assay may be performed using less of the costly particle reagent than was previously required.

EXAMPLE 3

Direct Crossmatch Test for ABO Group using a Reaction Vessel with Antibodies previously coated thereon Firstly, an antiserum with respect to A antigens on the surface of blood cells is coated in the recess 4 of a reaction vessel as shown in FIGS. 1A–1C using the method described below.

Standard anti-A serum (Orso Co.) is diluted to 1/10 with 10 mM Tris-HCl buffer solution, pH 9, containing 0.15M NaCl. 2 $\mu$l of the diluted solution is dropped to reaction zone 5 arranged on the polyethylene lower plate 1. After dropping, the diluted solution is incubated at 37° C. for 1 hour while maintaining humid conditions so that it does not dry out. The reaction zone 5 is then washed by dropping 1 $\mu$l of 10 mM phosphate buffer solution, pH 7.2, containing 0.15M NaCl. After removing the wash solution by gently shaking lower plate 1, 1 ml of 10 mM phosphate buffer solution, pH 7.2, containing 3% (w/v) of bovine serum albumin and 0.15 M NaCl are dropped in around reaction zone 5, and the lower plate is incubated at room temperature while maintaining humid conditions for 1 hour. By this procedure, the area of the reaction zone which adsorbs blood cells non-specifically is blocked. After incubation, reaction zone 5 is again washed using 2 ml of 10 mM phosphate buffer solution, pH 7.2, containing 0.15 M NaCl. If the lower plate is to be kept for a long period, 0.02% (w/v) NaN$_3$ is added to the final wash solution, and the lower plate is kept at 4° C. after washing. Moreover, in addition to lower plate 1, upper plate 3 is also treated so that non-specific reaction with blood cells does not occur. This is done by leaving the upper plate 3 at room temperature for 1 hour in 10 mM phosphate buffer solution, pH 7.2, containing 3% (w/v) bovine serum albumin and 0.15 M NaCl and washing it with 10 mM phosphate buffer solution, pH 7.2, containing 0.15 M NaCl. If the upper plate is to be left for a long period, 0.02% (w/v) NaN$_3$ is added to the final wash solution, and the upper plate is kept at 4° C. as in the case of the lower plate. In addition to this lower plate 1 and upper plate 3, the reaction vessel is assembled using 2 spacers 2 which are fixed by means of double-sided adhesive tape or adhesive.

We shall now describe the direct crossmatch test of ABO group using this reaction vessel wherein an antiserum has been coated.

First, a sample of blood is separated into a blood cell component 13 and blood serum component 12 by centrifugation or another suitable method. If the blood was treated with an anticoagulant such as heparin, the blood serum component 12 will be plasma. Next, 2 $\mu$l of the sedimented blood cell component 13 and 198 $\mu$l of a solution 14 are mixed in a test tube 17 to prepare a 1% blood cell suspension. In this case, solution 14 is physiological saline. This blood cell suspension 16 is then introduced by means of a pipette 18 to reaction zone 5 of reaction vessel 19 wherein anti-A serum has been coated as described above. After pipetting, the vessel is incubated at about 36° C. for 10 min, care being taken not to shake the vessel.

After the reaction is complete, the distribution pattern of particles sedimented in reaction zone 5 of reaction vessel 19 is observed using the same method as in Example 1. If there are A antigens on the surface of the blood cells in the sample, the cells combine with the anti-A serum that was coated in the reaction vessel, and the blood cells are uniformly distributed practically all over reaction zone 5 including recess 4. The pattern which appears in this case is therefore of the type shown in FIG. 2A. If on the other hand there are no A antigens on the surface of the cells in the sample, the blood cells do not combine with the anti-A serum coated in the reaction vessel, and the cells move freely down the sloping walls of conical recess 4. In this case, therefore, the distribution of blood cells gives a pattern of the type shown in FIG. 2B. In this way, from the difference in the distribution pattern after reaction, it is possible to determine the presence or absence of A antigens on the surface of blood cells in the sample. The presence or absence of B antigens on the surface of the blood cells may be determined in the same way by measuring the reactivity of the sample with respect to anti-B serum.

From its measured reactivity with respect to anti-A serum and anti-B serum, the blood group of the sample can be determined. If the blood cells in the sample showed an antigen-antibody reaction with respect to both anti-A serum and anti-B serum, the blood group of the sample is AB; if there was a reaction only with respect to anti-A serum, the blood group of the sample is A; if there was a reaction only with respect to anti-B serum, the blood group of the sample is B; while if there was no reaction to either serum, the blood group of the sample is O.

The determination of blood group, which previously required 60 minutes, can be accomplished in about 10 minutes using the reaction vessel of this invention.

EXAMPLE 4

Assay for Anti-HIV Antibody using a Reaction Vessel with Antigens previously coated thereon Assays for various antibodies can be carried out using a reaction vessel wherein antigens have been coated instead of the anti-serum used in Example 3. We shall describe an assay for anti-HIV antibody, using such a method with reference to FIG. 12.

Figure 12:
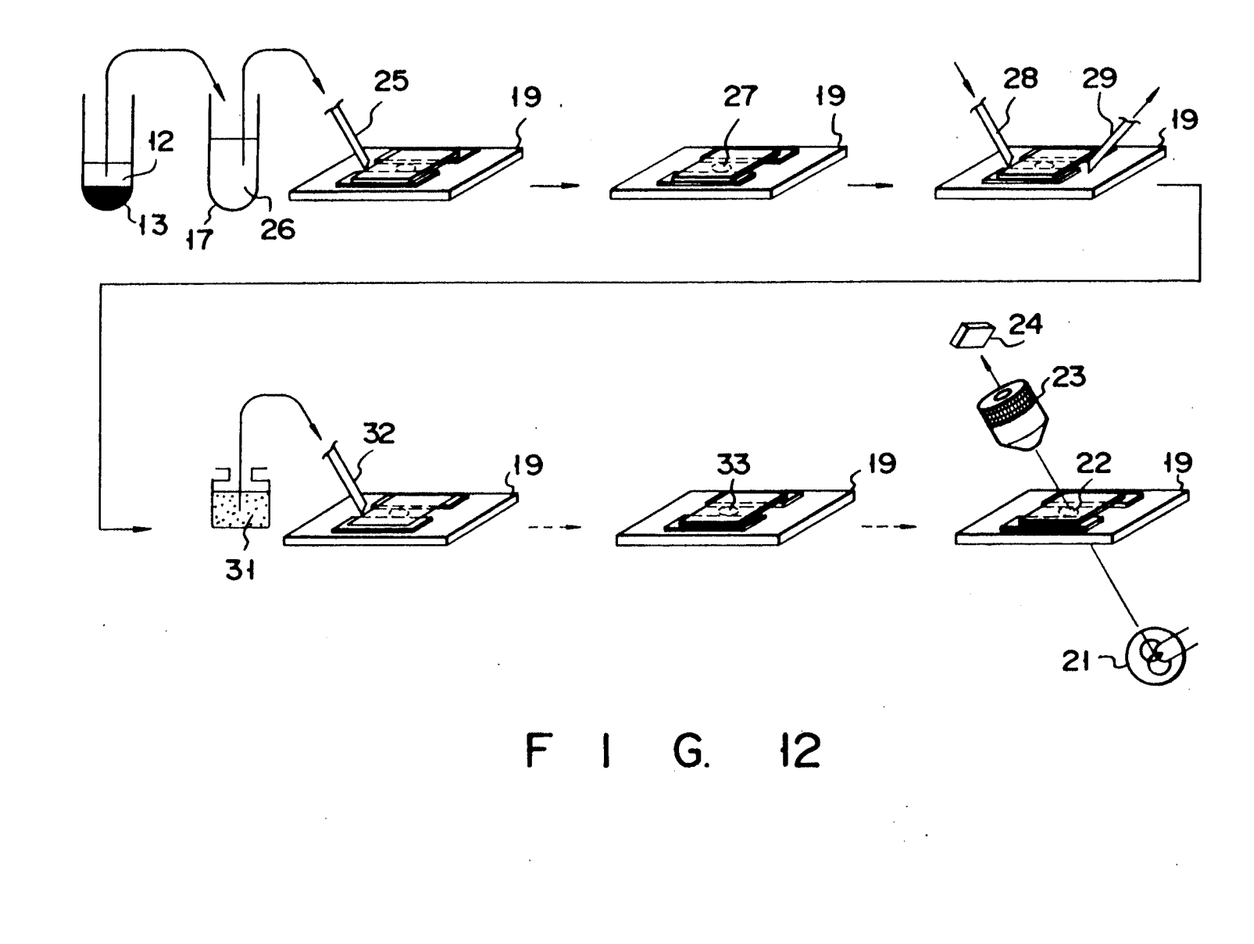
FIG. 12 is a view showing another process in an agglutination test using the reaction vessel shown in FIGS. 1A-1C.

Firstly, using a similar method to that described in Example 3, HIV antigens are coated in the reaction zone 5 of the reaction vessel. The HIV antigens coated in the reaction vessel may be chemically synthesized HIV virus surface antigens, HIV recombinant proteins produced by *Escherichia coli*, or the HIV virus itself.

Next, a sample of blood is separated into a blood cell component 13 and blood serum component 12 by centrifugation or another suitable method. If the blood was treated with an anticoagulant such as heparin, the blood serum component 12 will be plasma. 2 $\mu$l of the serum component obtained was removed in a test-tube 17, then 18 $\mu$l of physiological saline was added and mixed with it. 5 $\mu$l of this diluted serum solution 26 was pipetted by means of pipette 18 to a reaction vessel 19 wherein HIV antigens had been coated. After pipetting, the reaction vessel was incubated at 37° C. for 2 min (27). Following the reaction, physiological saline for washing was introduced by nozzle 28 into reaction zone 5 of reaction vessel 19, and waste liquid was aspirated simultaneously by nozzle 29 from the opposite side. By this procedure the reaction zone 5 can be washed, and the serum component which did not react with the antigen coated in reaction vessel 19 can be washed out.

Next, 5 $\mu$l of particle reagent 31 to which goat anti-human antibodies had been coated, was pipetted by means of pipette 32 into the reaction vessel and the vessel was incubated at 37° C. for 10 min. The anti-human antibodies used here may also be monoclonal antibodies derived from mouse or the like, or a substance such as protein A which binds to antibodies. Further, the particles on which the antibodies are coated may be red blood cells fixated by glutaraldehyde or the like, or synthetic particles such as polystyrene.

After the reaction is complete, the particle distribution is observed by the same method as that of Example 1. If there are antibodies against for HIV in the serum of the sample, they combine with the HIV antigens coated in the reaction vessel, and the particles to which anti-human antibodies have been coated combine with the antibodies which have combined with the antigens. The particle distribution is therefore of the type shown in FIG. 2A. If on the other hand there are no HIV antibodies in the serum of the sample, the particles roll freely down the sloping walls of recess 4 of the reaction vessel without causing any reaction. The particle distribution is therefore of the type shown in FIG. 2B.

By varying the type of antigen coated in the reaction vessel, antibodies against for viruses other than HIV such as HTLV-1 or HTLV-II or for bacteria may also be detected.

The antibody usually has 2-10 antigen binding sites. Particles to which the same antigen has been coated as the antigen coated in the reaction vessel, may therefore also be used as particle reagent 31.

What is claimed is:

1. A reaction apparatus for carrying out agglutination reactions, comprising:

a lower plate having an inner wall, said inner wall constructed so as to define at least one recess;

a transparent plate mounted adjacent to said lower plate, said transparent plate comprising a flat surface and communicating with said inner wall of said lower plate;

at least a portion of said inner wall of said lower plate, and said transparent plate, being spaced apart from one another over at least an area of said at least one recess;

means for maintaining said lower plate and said transparent plate positioned relative to each other so as to define a sample inlet channel space between said inner wall of said lower plate and said transparent plate, said sample inlet channel space being in flow communication with said at least one recess and being constructed so as to aspirate a sample into said at least one recess by capillary action, said at least one recess further constructed so as to allow agglutination reactions to form sedimented particle reactions; and said transparent plate constructed so as to restrict the amount of sample contacting said sample inlet channel space, thereby regulating particle pattern formation within said at least one recess.

2. A reaction apparatus according to claim 1, wherein said maintaining means comprises at least one spacer means between said lower plate and said transparent plate for maintaining said lower plate and said transparent plate spaced apart from one another.

3. A reaction apparatus according to claim 1, wherein said at least one recess comprises a plurality of recesses.

4. A reaction apparatus according to claim 1, wherein said at least one recess has a conical shape.

5. A reaction apparatus according to claim 1, wherein said at least one recess comprises an inner wall having antigens or antibodies coated thereon.

6. A reaction apparatus according to claim 1, wherein said at least one recess comprises sloped walls.

7. A reaction apparatus according to claim 1, wherein said at least one recess has a hemispherical shape.

8. A reaction apparatus for carrying out agglutination reactions, comprising:
- a lower plate having an inner wall, said inner wall constructed so as to define at least one groove, said at least one groove constructed so as to extend over at least a portion of said lower plate;
- a flat transparent plate mounted adjacent to said lower plate and communicating with said inner wall of said lower plate so as to cover at least a portion of a length of said at least one groove;
- at least a portion of said inner wall of said lower plate, and said transparent plate, being spaced apart from one another over at least a portion of the length of said at least one groove;
- means for maintaining said lower plate and said transparent plate positioned relative to each other so as to define a sample inlet channel space between said inner wall of said lower plate and said transparent plate, said sample inlet channel space being in flow communication with said at least one groove and being constructed so as to aspirate a sample into said at least one groove by capillary action, said at least one groove further constructed so as to allow agglutination reactions to form sedimented particle reactions in a portion thereof which is covered by said transparent plate; and
- said transparent plate constructed so as to restrict the amount of sample contacting said sample inlet channel space, thereby regulating particle pattern formation within said at least one groove.

9. A reaction apparatus according to claim 8, wherein said maintaining means comprises at least one spacer means between said lower plate and said transparent plate for maintaining said lower plate and said transparent plate spaced apart from one another.

10. A reaction apparatus according to claim 8, wherein said at least one groove comprises a plurality of grooves.

11. A reaction apparatus according to claim 8, wherein said at least one groove has a U-shaped cross-section.

12. A reaction apparatus according to claim 8, wherein said at least one groove has a V-shaped cross-section, said at least one groove further comprising an inner surface, wherein said inner surface is constructed so as to define a continuously varying slope angle over at least a portion of said lower plate.

13. A reaction apparatus according to claim 8, wherein antigens or antibodies are coated on said inner surface of said at least one groove.

14. A reaction apparatus according to claim 8, wherein said at least one groove has a V-shaped cross-section.

* * * * *